United States Patent
Henriquez Peralta

(10) Patent No.: US 11,884,861 B2
(45) Date of Patent: Jan. 30, 2024

(54) **SOIL-STABILISING COMPOSITION COMPRISING *AZOBACTER VINELANDII*, *ACIDITHIOBACILLUS FERROOXIDANS*, ALGINASE, AND CALCIUM CHLORIDE; METHOD FOR STABILISING SOILS; METHOD FOR PREPARING STABILISED PATHS; USE OF THE SOIL-STABILISING COMPOSITION**

(71) Applicant: Hydra Research SPA, Santiago (CL)

(72) Inventor: Jonathan Pedro Henriquez Peralta, Santiago (CL)

(73) Assignee: Hydra Research SPA, Santiago (CL)

( * ) Notice: Subject to any disclaimer, the term of this patent is extended or adjusted under 35 U.S.C. 154(b) by 448 days.

(21) Appl. No.: 16/958,591

(22) PCT Filed: Dec. 3, 2018

(86) PCT No.: PCT/CL2018/050120
§ 371 (c)(1),
(2) Date: Jun. 26, 2020

(87) PCT Pub. No.: WO2019/126887
PCT Pub. Date: Jul. 4, 2019

(65) Prior Publication Data
US 2021/0002553 A1  Jan. 7, 2021

(30) Foreign Application Priority Data
Dec. 28, 2017  (CL) .................................. 3464-2017

(51) Int. Cl.
| | |
|---|---|
| *C09K 17/42* | (2006.01) |
| *C09K 3/22* | (2006.01) |
| *C12N 1/20* | (2006.01) |
| *E01C 19/48* | (2006.01) |
| *E01C 21/00* | (2006.01) |
| *E02D 3/12* | (2006.01) |
| *E02D 3/02* | (2006.01) |

(52) U.S. Cl.
CPC ................ *C09K 17/42* (2013.01); *C09K 3/22* (2013.01); *C12N 1/20* (2013.01); *E01C 19/4806* (2013.01); *E01C 21/00* (2013.01); *E02D 3/123* (2013.01)

(58) Field of Classification Search
CPC .......... C09K 17/42; C09K 3/22; C09K 17/40; C12N 1/20; C12N 9/88; E01C 19/4806; E01C 21/00; E02D 3/123
See application file for complete search history.

(56) References Cited

FOREIGN PATENT DOCUMENTS

| | | | |
|---|---|---|---|
| EP | 0078643 A1 * | 5/1983 | |
| WO | WO-2014057443 A2 * | 4/2014 | ............... C12N 1/20 |

OTHER PUBLICATIONS

Xiao, Lin, et al. "A novel alginate lyase with high activity on acetylated alginate of *Pseudomonas aeruginosa* FRD1 from *Pseudomonas* sp. QD03." World Journal of Microbiology and Biotechnology 22.1 (2006): 81-88. (Year: 2008).*

Ivanov, Volodymyr, and Jian Chu. "Applications of microorganisms to geotechnical engineering for bioclogging and biocementation of soil in situ." Reviews in Environmental Science and Bio/Technology 7.2 (2008): 139-153. (Year: 2008).*

Huixin Xiong, Yuehua Liao, and Lixiang Zhou Environmental Science & Technology 2008 42 (23), 8681-8686 DOI: 10.1021/es801646j (Year: 2008).*

KEGG; https://www.genome.jp/dbget-bin/www_bget?ec:4.2.2.3; accessed Nov. 8, 2022 (Year: 2022).*

* cited by examiner

*Primary Examiner* — Lora E Barnhart Driscoll
*Assistant Examiner* — Candice Lee Swift
(74) *Attorney, Agent, or Firm* — Quarles & Brady LLP

(57) ABSTRACT

A formulation for stabilizing soils is described comprising bacteria, enzymes and cations, wherein the bacteria preferably correspond to *Azotobacter vinelandii* and *Acidithiobacillus ferrooxidans*, the enzyme preferably corresponds to an alginase and the cations are preferably provided in the form of calcium chloride. A method for stabilizing soils; a method for preparing stabilized paths; and use of the soil-stabilizing composition are also described.

10 Claims, No Drawings

SOIL-STABILISING COMPOSITION COMPRISING *AZOBACTER VINELANDII*, *ACIDITHIOBACILLUS FERROOXIDANS*, ALGINASE, AND CALCIUM CHLORIDE; METHOD FOR STABILISING SOILS; METHOD FOR PREPARING STABILISED PATHS; USE OF THE SOIL-STABILISING COMPOSITION

FIELD OF THE INVENTION

The present invention refers to a formulation for stabilizing soils, said soil-stabilizing formulation comprising bacteria, enzymes and cations, wherein bacteria preferably correspond to *Azotobacter vinelandii* and *Acidithiobacillus ferrooxidans*, the enzyme preferably corresponds to an alginase, and the cations are preferably provided in the form of calcium chloride.

In other aspect of the invention, a method of soil stabilization is provided that includes contacting a soil-stabilizing formulation with a soil and letting the composition act in the soil, obtaining a stabilized soil, where said soil-stabilizing formulation preferably comprises *Azotobacter vinelandii*, *Acidithiobacillus ferrooxidans*, alginase and calcium chloride.

In another aspect of the invention, a method is provided to prepare a stabilized path that comprises reconditioning the soil by incorporating filler or structural material, homogeneously incorporating the soil-stabilizing composition of the invention, mixing with the filler material or with the already extracted soil, spreading the homogenized material on the road to be built, wetting, and mechanically compacting the area of the road to be constructed.

In still another aspect of the invention, the use of a composition that contains at least *Azotobacter vinelandii*, *Acidithiobacillus ferrooxidans*, alginase and calcium chloride is described, for stabilizing soils and constructing stabilized paths.

BACKGROUND

From the point of view of engineering, the concept of soil includes loose or moderately cohesive deposits such as gravel, sand, clay or any mixture thereof.

In this sense, soils can be classified as cohesive or non-cohesive. Cohesive soils contain small particles wherein surface electrochemical effects prevail, so that particles tend to agglomerate (water/particle interaction) in plastic soils such as clays. The main characteristic of cohesive soils is their plasticity and their ability to expand and contract under different humidity and temperature contents.

On the other hand, non-cohesive soils are composed of relatively large particles that do not tend to agglomerate or adhere. These soils are also called granular soils (sands, gravel and silt).

In Chile, more than 70% of the roads comprise unpaved paths, which are damaged at an early stage by vehicle traffic and by the loss of soil moisture.

For this reason, and in order to use these unpaved paths as traversable roads in the medium and in the long term, they are stabilized with different products by a process called soil stabilization.

In public roads, soil stabilizers must comply with the regulatory conditions established by the Ministry of Public Works, (Ministerio de Obras Públicas in Chile), and/or in other countries, among them those regarding geodesic, topographic, hydrologic, geotechnical aspects, hydraulics, transport of sediments, traffic demand and characteristics, and environmental aspects (impact and mitigation), as well as safety standards, control of fine grains, and they must improve load capacity and water resistance when faced by different types of soil.

Soil stabilization is the process by which a soil existing in a given area maintains its natural properties when confronted by external factors such as erosion, environmental change and freight transport. In this context, a soil is stabilized with a view to exploit its attributes, obtaining a more stable and longer-lasting rolling surface.

Soil stabilization generally comprises a treatment that is usually chemical or mechanical and maintains and improves stability of a soil body for engineering purposes.

Soil stabilization methods can be classified as follows:
mechanical stabilization (Compaction);
physical stabilization;
chemical stabilization; and
chemical stabilization employing new technology.

Mechanical stabilization consists in repeatedly and mechanically applying a short mechanical action on a soil body in order to increase its shear resistance. Among mechanical stabilization procedures are kneading, load impacts, static pressure, vibration and combined methods.

On the other hand, physical stabilization is used to improve the soil in a particular area, producing a number of physical changes. There are several techniques such as mixing soils together with compaction, geotextiles, vibroflotation and previous consolidation.

Despite its widespread use, it is known in the art that mechanical stabilization has several disadvantages, among them a limited durability of the stabilization (generally less than a year) depending on the type of vehicle traffic, the weather, vehicle tonnage, the high cost that depends on the type of soil, for example with clayey paths.

Alternatively, on mechanically stabilized roads it is necessary to use low-tonnage vehicles because they deteriorate faster.

Chemical stabilization was developed in order to remedy the disadvantages of mechanical and physical methods; it comprises the addition of specific chemical stabilizing agents, producing a chemical reaction of the stabilizing product with the soil, in order to obtain a modification of the soil properties and characteristics, providing a better response to the mechanical load requirements to which a well trodden path will be subjected.

Chemical stabilizers can be divided into those that provide cohesive force to a soil providing covering or waterproofing to the soil grains, those that provide durability and strength by a cementitious adherence between soil particles, and those that are applied to cohesive soils, generating an alteration in the nature of the water-clay system, thereby decreasing plasticity, volume changes, and increasing resistance.

The best-known chemical stabilizers are Portland cement, lime, asphalt, sodium chloride, magnesium chloride hexahydrate (bischofite) and calcium chloride.

More frequently, unpaved paths and soils are chemically stabilized with concrete and asphalt (Asi, I. et al. 2002. Geotechnical Testing Journal. Vol. 25, No. 2, pp. 168-176). Despite their durability, said stabilizers are costly to apply, which makes their implementation costly and time-consuming.

As the most available option in the market, especially in Chile, bischofite (molecular formula $MgCl_2 \times 6H_2O$) is used in road stabilization (Vergara Ravanal, Raúl Andrés. 2011. Estabilización y control de polvo con bischofita), together with other commonly used stabilizers such as calcium chloride, sodium chloride, among others (Durotoye T. O, Akinmusuru J. O. 2016. International Journal of Research in Engineering and Technology. Vol 5. pp. 11-16).

In spite of the known advantages of chemical stabilization over physical stabilization, the former has still deficiencies that have not been remedied in the art, mainly, its environmental impact and low efficiency in wet environments, given its high solubility in water.

Considering then the technical disadvantages of chemical stabilizers, new technologies have been developed that include ion exchange agents (ionic stabilization), polymers, and enzymes, among others.

Ionic stabilization is generally applied to fine soils, producing a strong ionic interchange with the mineral clay particles in the soil. In this way, the absorption water is displaced occupying the vacant ionic space, blocking water absorbency of the active particles, which are responsible for the swelling and the loss of their bearing capability. Then, the particles that have become free from the electrostatic charges that keep them apart and the water particles that are close to them, approach and agglomerate increasing in this way the frictional load capacity between the particles, resulting in an increase in compaction density.

On the other hand, polymers are used because they have a good mechanical resistance due to the large polymer chains that attract soil particles through the formation of a network that surrounds the soil surface (Teresa Lopez Lara et al. 2010. Volume 11(3). pp. 159-168). These intermolecular attraction forces depend on the chemical composition of the polymer. Their use to stabilize soils generates a high resistance to traction, fatigue and impact of the treated soils. These products are generally used in asphalt rolling surfaces, in order to give them greater resistance, waterproofing and extension of their useful life.

Finally, the use of enzymes as soil stabilizers is known in the art. They catalyze degradation of the organic materials in the soil, positively altering their physical and chemical properties.

Enzymes have the advantage of being entirely biodegradable, in addition to their efficacy in the stabilization of clayey soils. After applying the enzyme, the clay particles present in the soil are no longer attracted by water, allowing water in the soil to drain freely and resulting in the settlement of clay particles (David Cedeño Plaza, 2013. Universidad Central de Ecuador).

Despite of the existence of a multiplicity of soil stabilization methods, the deficiencies existing in each one of them have not been addressed in the known art, mainly that they are not applicable to all types of soils; for example, some are hydroscopic, others emulsify, others strictly depend on the type of soil, slowing down the placement process because they must be premixed prior to use (as in the case of bischofite), and are generally expensive, representing approximately 40% of the construction costs of a road.

The present invention overcomes said disadvantages, providing a greater compaction capacity; it is less costly than methods generally used in the art, its operational costs are lower, is easy to apply, non-toxic, biodegradable and has a high durability.

BRIEF DESCRIPTION OF THE INVENTION

The present invention corresponds to a new soil-stabilizing product comprising at least bacteria, enzymes and cations, where the bacteria preferably correspond to *Azotobacter vinelandii* and *Acidithiobacillus ferrooxidans*, the enzyme is preferably alginase, and the cations are preferably provided in the form of calcium chloride. The soil-stabilizing composition is preferably comprised of *A. vinelandii*, calcium chloride, *A. ferrooxidans*, and the enzyme alginase.

The present composition, object of the invention, has applications in road construction, tailing control, dust control and slope stabilization, and promotes improvements preferred, but not limited to improvements in soil compaction, dust control (DustKill), is non-toxic and environmentally friendly.

Together with the stabilizing composition described, which comprises at least *Azotobacter vinelandii, Acidithiobacillus ferrooxidans*, alginase and calcium chloride, an object of the present invention is to provide in addition a method of soil stabilization that comprises bringing a soil into contact with the composition of the invention to produce a stabilized soil, which generates an improvement in soil characteristics as an increased California Bearing Ratio (CBR), promotes particle cohesion in adherent and non-adherent materials, and maintains the natural colour of the soil, where CBR is known in the art and is defined as:

CBR (%)=(test unit load/standard unit load)*100.

Another aspect of the present invention is to provide a method for preparing a stabilized road that comprises reconditioning the soil by the incorporation of filler or structural material, homogeneously incorporating the soil-stabilizing composition that preferably comprises *Azotobacter vinelandii, Acidithiobacillus ferrooxidans*, alginase and calcium chloride, mixing said homogeneous stabilizer with the filler material or with the already extracted soil, spreading the homogenized material on the road to be constructed, wetting, and mechanically compacting the area of the road to be constructed.

Furthermore, the use of the composition of the invention, which comprises at least *Azotobacter vinelandii, Acidithiobacillus ferrooxidans*, alginase and calcium chloride, is described for stabilizing cohesive and non-cohesive soils, improving soil stability characteristics.

DETAILED DESCRIPTION OF THE INVENTION

A composition comprising at least *Azotobacter vinelandii, Acidithiobacillus ferrooxidans*, alginase and calcium chloride is provided, which stabilizes soils when making contact with said soil.

In a preferred embodiment, the soil-stabilizing composition is a bi-component formulation that comprises solution A and solution B.

In a preferred embodiment, solution A comprises as a percentage by weight based on the total weight of solution A, approximately 8% to 15% *Azotobacter vinelandii*, a percentage by volume based on the total volume of solution A of 11-19% *Acidithiobacillus ferrooxidans*, and an approximate concentration of alginase up to approximately 5% by weight based on the total weight of solution A.

In said preferred embodiment, solution B comprises, as a percentage by weight based on the total weight of solution B, approximately 20% to 35% calcium chloride. Such preferred proportions are understood as illustrative by an expert in the art, and do not correspond in any way to limitations of the present invention, since said conditions may be varied depending on the characteristics of the soil, or on the weather conditions.

In an even more preferred embodiment, solution A comprises as a percentage by weight based on the total weight of solution A, approximately 8% *Azotobacter vinelandii*, a percentage by volume based on the total volume of solution A of 15% *Acidithiobacillus ferrooxidans*, and an approximate concentration of alginase of about 5% by weight based on the total weight of solution A.

In said even more preferred embodiment, solution B comprises approximately 20% of calcium chloride as a percentage by weight based on the total weight of solution B.

In some preferred embodiments, the alginase enzyme is a non-purified native or recombinant enzyme. In yet another preferred embodiment, the alginase enzyme is a purified native or recombinant enzyme. In an even more preferred embodiment, the alginase is a *Pseudomonas aeruginosa* alginase. An expert in the art will understand that said *Pseudomonas aeruginosa* alginase is one of multiple options, and can indiscriminately be exchanged for another alginase with the activity and required reaction conditions similar to those of *Pseudomonas aeruginosa* alginase.

In another aspect of the invention, a method of road stabilization is provided which comprises adding the soil-stabilizing composition of the invention to a soil, obtaining as a result a stabilized soil.

In a preferred embodiment, the method of soil stabilization of the present invention comprises the stages of:
 a) adding solution A of the present invention to the water tank of a first cistern truck;
 b) adding solution B of the present invention to the water tank of a second cistern truck;
 c) pouring the diluted solution from stage (a) into a soil; and then
 d) pouring the diluted solution from stage (b) into a soil, wherein the diluted solution from stage (a) had previously been poured into that soil, as specified in stage (c).

Preferably, to obtain the diluted solutions from stages (a) and (b) of the method of the present invention, the above described solutions A and B of the present invention are diluted at a ratio of approximately 1 litre of solution per 1000 litres of water, wherein said diluted solutions from stages (a) and (b) are entirely poured into the soil. An expert in the art will understand that other ratios are possible for the method object of the present invention obtaining similar results.

Preferably, the soil to be stabilized is additionally compacted after stage (d) by methods known in the art, for instance, with a roller, in order to compress the soil particles even further, improving the stabilizing effect of the soil-stabilizing composition, object of the present invention.

In another embodiment that is even more preferred, a method is provided to prepare a stabilized road that comprises the stages of:
 a) depending on the granulometric analysis, reconditioning the soil by incorporating filler or structural material, to a depth of approximately 10 to 15 cm;
 b) homogeneously incorporating the soil-stabilizing composition of the invention;
 c) mixing the soil stabilizer with filler material or with the same already extracted soil;
 d) spreading the previously homogenized material on the road to be constructed;
 e) wetting, where the amount of water required for wetting will depend on the result of the modified Proctor test; and
 f) mechanically compacting the area of the road to be built, where mechanical compaction is preferably accomplished with a roller.

Preferably, the surface must be free from potholes and longitudinal distortions (pitting and material accumulation), and transversal distortions (undulations and calamines), leaving longitudinal side indentations to allow drainage of rainwater in order to prevent damaging the rolling surface, before applying the soil-stabilizing composition of the invention.

Preferably, compaction of the soil to be treated with the stabilizing composition of the invention should be at least 95%.

In general, the soil-stabilizing composition of the present invention, the method of soil stabilization and the method for preparing a stabilized road of the present invention, improve at least one property of the soil, such as its volumetric stability, resistance, permeability, compressibility and durability. Said improved properties correspond to only one group of those identified, and do not limit the positive effects of the present invention for soil stabilization.

In a preferred aspect, the composition of the present invention and the method of soil stabilization improve CBR, resulting in a value of approximately 136%.

In yet another preferred aspect, the composition and method of the invention produce a soil stabilized for approximately 1 to 1.5 years.

The term "improving volumetric stability" used is defined as maintaining the soil volume relatively constant for the purpose of using it for road construction; the increase of which is desirable for soils susceptible to liquefaction, expansive and collapsible, such as clayey soils.

"Soil resistance", which is significantly improved by the application of the composition of the invention, is defined on the basis of the parameters known for the technique in the field of soil stabilization, among them, California Bearing Ratio or CBR.

"Permeability" is understood as the capability of a medium to transfer water or other substances. In soils, permeability is due to the existence of interconnected pores. Said factor is improved by applying the composition of the invention, since soil compaction generally generates a sealing of the surface layer of the roads, making water permeability impossible. The composition of the invention does not affect permeability in a negative way, allowing water to flow and preventing water from forming puddles on the road surface.

"Compressibility" is defined as the degree in which the volume of the soil body decreases under the effect of a load. It is a property that in itself affects others, such as permeability, modifying soil resistance to shear or causing landslides. Compressibility is proportional to the plasticity index, so the higher the plasticity index, the higher the compressibility of the soil.

"Durability" is associated to resistance to weather conditions, such as the erosion or abrasion caused by traffic, which is improved when applying the composition object of this invention, since the higher the compaction percentage, the greater the particle cohesion generated, increasing road support (CBR), impacting on durability of the road.

The composition and method object of the present invention can be applied to roads and soils of multiple natures. Non-limiting examples of such roads are rural tracks, working paths, tunnels, parking lots, landing strips, internal farm paths, secondary roads, agricultural tracks, beaches and esplanades, and highway shoulders.

Ways to Implement the Invention

Preferred ways to implement the invention are described below, in addition to illustrative experimental results related to the invention. Notwithstanding the above, an expert in the field should understand that these examples are illustrative, and in no way correspond to limitations of the scope of the present invention.

Example 1

Method to Prepare the Soil-Stabilizing Composition

The culture of *A. vinelandii* is carried out under standard conditions known in the art. Particularly for this example, bacteria were grown at 30° C. for two days, in standard culture media for *A. vinelandii* that contained the components described in Table 1 per 1000 millilitres of the total medium. at a pH of approximately 7.3 (Table 1)

Table 1: Culture Medium for *A. vinelandii*.

TABLE 1

Culture medium for *A. vinelandii*.

| Component | Amount per 1000 litres of total culture medium |
|---|---|
| Glucose | 5.00 g |
| Manitol | 5.00 g |
| $CaCl_2\,x2H_2O$ | 0.10 g |
| $MgSO_4\,x7H_2O$ | 0.10 g |
| $Na_2MoO_4\,x2H_2O$ | 5.00 mg |
| $K_2HPO_4$ | 0.90 g |
| $KH_2PO_4$ | 0.10 g |
| $FeSO_4\,x7H_2O$ | 0.01 g |
| $CaCO_3$ | 5.00 g |
| Agar | 15.00 g |

The culture of *A. ferrooxidans* is also carried out under standard conditions known in the art. Particularly for this example, said culture of *A. ferrooxidans* was carried out growing the bacteria at 25° C. from three to seven days in standard culture media for *A. ferrooxidans* at a pH of approximately 1.8, which is obtained by mixing 950 mL of Solution 1, with 50 mL of Solution 2, and 1 mL of Solution 3, according to Table 2

TABLE 2

Culture medium for *A. ferrooxidans*.

Solution 1

| Component of Solution 1 | Amount |
|---|---|
| $(NH_4)_2SO_4$ | 132.0 mg |
| $MgCl_2\,x6H_2O$ | 53.0 mg |
| $KH_2PO_4$ | 27.0 mg |
| $CaCl_2\,x2H_2O$ | 147.0 mg |

TABLE 2-continued

Culture medium for *A. ferrooxidans*.

Solution 2

| Component of Solution 2 | Amount |
|---|---|
| $FeSO_4\,x7H_2O$ | 20.0 g |
| $H_2SO_4$ 0.25N | 50.0 mL |

Solution 3

| Component of Solution 3 | Amount |
|---|---|
| $MnCl_2\,x2H_2O$ | 62.0 mg |
| $ZnCl_2$ | 68.0 mg |
| $CoCl_2\,x6H_2O$ | 64.0 mg |
| $H_3BO_3$ | 31.0 mg |
| $Na_2MoO_4$ | 10.0 mg |
| $CuCl_2\,x2H_2O$ | 67.0 mg |

In turn, alginase is prepared as it is known in the art. For illustrative purposes, alginase preparation is described as follows:
a) adding 50 mL of filtered distilled water to a 100 mL beaker;
b) adding approximately 20 to 50 mg of alginase to the 50 mL of water, and agitating at least for 5 minutes;
c) adding the alginase solution from stage (b) to 2 litres of distilled water, while maintaining constant agitation;
d) adding 100 ml of a mixture with a volume ratio of the culture of *A. vinelandii* to the volume of the culture of *A. ferrooxidans* of approximately 4:1, ensuring that it is vigorously agitated;
e) allowing to stand at least for 3 hours and ideally overnight, and confirming that the solution loses viscosity by conventional methods known in the art; and
f) starting agitation again for an additional 30 minutes, and stopping agitation afterwards.

The solution obtained by mixing the bacterial cultures with the reconstituted alginase corresponds to undiluted solution A.

The concentrated solution B of the present invention is prepared by means known to an expert in the art, and corresponds to a 70% weight/weight calcium chloride solution, in distilled water.

Example 2

Method to Apply the Soil-Stabilizing Composition

Generally, to apply this stabilizer, approximately 1 litre of solution A or solution B was diluted in approximately 1,000 litres of water. In general, 1 litre of each concentrated solution A and B allows stabilizing approximately 200 m2 of compacted soil.

The stabilization results of the composition of the invention, obtained by the method of stabilization that is also an object of the invention, are illustrated in Table 3, below:

TABLE 3

Results of soil stabilization by the composition of the invention, with respect to other stabilizers.

| Properties | Bischofite | Asphalt | Lime | Cement | Salts in general | Composition of the invention |
|---|---|---|---|---|---|---|
| Compacting capacity (CBR) | 106% | 102% | 98% | 97% | 105% | 136% |
| Economic costs | High economic values | High economic values | High economic values | High economic values | High economic values | Low economic cost (60% compared to Bischofita) |

TABLE 3-continued

Results of soil stabilization by the composition of the invention, with respect to other stabilizers.

| Properties | Bischofite | Asphalt | Lime | Cement | Salts in general | Composition of the invention |
|---|---|---|---|---|---|---|
| Toxicity (Environment) | Possible contamination of crops adjoining the road | Possible contamination of crops adjoining the road | Possible contamination of crops adjoining the road | Possible contamination of crops adjoining the road | Possible contamination of crops adjoining the road | Non-contaminant |
| Applicability | Climatic conditions of temperature and rainfall should be considered in terms of their application | Not applicable | Climatic conditions of temperature and rainfall should be considered in terms of their application | | Climatic conditions of temperature and rainfall should be considered in terms of their application | Can be applied at any time |
| Operating costs (Machinery, Transport, Labour, etc.) | High operating costs | High operating costs | High operating costs | High operating costs | High operating costs | Very low operating costs (70% compared to Bischofite) |
| Safety | Slippery surfaces in the presence of fog, rain, surface moisture, among others | Not applicable | Slippery surfaces in the presence of fog, rain, surface moisture, among others | | Slippery surfaces in the presence of fog, rain, surface moisture, among others | Does not affect traffic safety |

Bearing ratio or CBR is measured as a percentage (%) and at 0.2" penetration in a saturated sample and pre-compacted to a density equal to or over 95% of the M.C.D.D. obtained in the Modified Proctor test (NCh1534/2).

In areas where the average annual precipitation is less than 50 mm, CBR test is conducted on non-saturated samples, provided that it is previously authorized by the Supervisor.

With regard to compaction to the sub-base, it is compacted until the density obtained is not less than 95% of the M.C.D.D. obtained in the Modified Proctor test (NCh1534/2).

The invention claimed is:

1. A soil-stabilizing composition comprising:
(i) a solution A comprising *Azotobacter vinelandii*, *Acidithiobacillus ferrooxidans* and a *Pseudomonas aeruginosa* alginase; wherein solution A comprises from 8% to 15% *Azotobacter vinelandii* as a percentage by weight based on the total weight of solution A, from 11% to 19% *Acidithiobacillus ferrooxidans* as a percentage by volume based on the total volume of solution A, and from greater than 0% to 5% of alginase as a percentage by weight based on the total weight of solution A; and
(ii) a solution B comprising cations in the form of calcium chloride; wherein solution B contains from 20% to 35% calcium chloride as a percentage by weight based on the total weight of solution B.

2. The soil-stabilizing composition of claim 1 wherein
(i) solution A comprises 8% *Azotobacter vinelandii*, as a percentage by weight based on the total weight of solution A, 15% *Acidithiobacillus ferrooxidans* as a percentage by volume based on the total volume of solution A, and 5% alginase as a percentage by weight based on the total weight of solution A; and
(ii) solution B contains 20% calcium chloride, as a percentage by weight based on the total weight of solution B.

3. A method of soil stabilization, comprising:
(a) adding the solution A of claim 1 to a water tank of a first cistern truck;
(b) adding the solution B of claim 1 to a water tank of a second cistern truck;
(c) pouring a diluted solution A from step (a) into a soil; and
(d) pouring a diluted solution B from step (b) into the soil, wherein the diluted solution from step (a) had previously been poured into said soil, as specified in step (c); and
(e) obtaining a stabilized soil.

4. The method of claim 3, comprising
independently adding 1 litre of solution A to 1000 litres of water contained in the water tank of the first cistern truck from step (a) to form diluted solution A, and
independently adding 1 litre of solution B to 1000 litres of water contained in the water tank of the second cistern truck from step (b) to form diluted solution B.

5. The method of claim 4 comprising compacting the soil after step (d).

6. The method of claim 5, wherein the compacting is accomplished with a roller.

7. A method to prepare a stabilized road, comprising:
(a) reconditioning the soil by the incorporation of filler or structural material, approximately at a depth of about 10 to 15 cm;
(b) homogeneously incorporating the soil-stabilizing composition of claim 1;
(c) mixing the homogeneous soil-stabilizing composition from step (b) with the filler material or with reconditioned soil from step (a);
(d) spreading the homogenized material from step (c) on the road to be constructed;
(e) wetting; and
(f) mechanically compacting an area of the road to be constructed.

8. The method of claim 7, wherein the mechanically compacting of stage (f) is accomplished by means of a roller.

9. The method of claim 8 comprising forming a stabilized road having a California bearing ratio (CBR) value of at least approximately 136%.

10. The method of claim 8 comprising forming a soil that is stabilized for 1 to 1.5 years.

\* \* \* \* \*